United States Patent [19]

Bernardi

[11] Patent Number: 4,798,540

[45] Date of Patent: Jan. 17, 1989

[54] INTEGRATED CT SCANNER GANTRY

[75] Inventor: Richard T. Bernardi, Prospect Heights, Ill.

[73] Assignee: Tokyo Shibaura Denki Kabushiki Kaisha, Kanagawa, Japan

[21] Appl. No.: 163,805

[22] Filed: Mar. 3, 1988

Related U.S. Application Data

[62] Division of Ser. No. 494,104, May 12, 1983.

[51] Int. Cl.⁴ .................. G03B 41/16; H01R 39/10
[52] U.S. Cl. .................................. 439/22; 378/15
[58] Field of Search ..................... 439/13, 16–30; 378/15

[56] References Cited

U.S. PATENT DOCUMENTS

| | | | |
|---|---|---|---|
| 2,645,759 | 7/1953 | Solari | 439/30 |
| 4,063,792 | 12/1977 | Lodge | 250/363 R |
| 4,090,079 | 5/1978 | Grassmann | 250/360 |
| 4,329,040 | 5/1982 | Lewis . | |
| 4,343,996 | 8/1982 | Kuipers | 378/21 |
| 4,402,085 | 8/1983 | Distler et al. | 378/15 |
| 4,644,573 | 2/1987 | Palermo et al. | 378/15 |

FOREIGN PATENT DOCUMENTS 2061028A 5/1981 United Kingdom .

*Primary Examiner*—Gary F. Paumen

*Attorney, Agent, or Firm*—Finnegan, Henderson, Farabow, Garrett, & Dunner

[57] ABSTRACT

An integrated CT scanner gantry assembly is provided wherein an open bore rotor is supported by a bearing assembly on an open bore stator. An x-ray assembly is mounted on the rotor and supplied with high voltage power during continuous rotation about the stator through use of a slip ring assembly which is mounted between the rotor and stator. The inside surface of the stator which faces a patient generally lies along the surface of a truncated cone to permit substantial tilting of the stator. Moreover, the stator and rotor have a cross section formed as a series of separated yet aligned steps to form two isolated cavities therebetween, one of the cavities housing the cathode of the slip ring and the other of the cavities housing the anode of the slip ring. The cavities can be filled with a gas or liquid high voltage insulating fluid and can be readily sealed to prevent leakage of said fluid. An x-ray assembly bracket is removably attachable to the rotor to support an x-ray source and x-ray optics in order to permit the x-ray source and x-ray optics to be assembled and aligned on the bracket at a location remote from the rotor and stator. The overlapping positions of the separated yet aligned steps relative to the x-ray source and optics assembly bracket reduces the cross-sectional area and overall gantry volume thereby providing comfortable patient access for whole body CT scanning.

3 Claims, 2 Drawing Sheets

INTEGRATED CT SCANNER GANTRY

This is a division of application Ser. No. 494,104, filed May 12, 1983.

BACKGROUND OF THE INVENTION

I. Field of the Invention

The present invention relates to the support structure, or gantry, for an x-ray computed tomography (CT) scanner or the like.

II. Description of the Prior Art

X-ray CT scanners are known which comprise an x-ray assembly mounted on a rotatable support. Such rotatable supports typically comprise a fixed stator and a rotor rotatably mounted thereon by means of a ring bearing. The stator and rotor are hollow bore to permit the whole body of a patient to lie along the axis of rotation of the rotor. An x-ray source and x-ray optics, including a shutter, wedges, and a collimator, are all individually mounted to the rotor and aligned with respect to one another.

The x-ray source requires access to high voltage. High voltage cables may be employed to connect a stationary high voltage source to the rotatable x-ray source. However, the cables then inhibit the degree by which the x-ray source may be rotated about the patient, and preclude continuous rotation of the x-ray source.

To provide continuous rotation of the x-ray source, known gantry assemblies employ the use of a standard high voltage slip ring assembly. Such a slip ring assembly is known to have its own rotor and stator structures which are supported on its own ring bearing. Known slip ring configurations require liquid or gas high voltage insulation and attendant seals. These seals are subject to repeated failure, requiring easy access to the seals and/or the ability to easily replace the entire slip ring assembly. Still further, known slip rings require electrical connection in a manner which results in close proximity crossing of high voltage wiring of one polarity with ring electrodes of the opposite polarity. Such crossings have the tendency to result in high voltage breakdown.

Such known slip ring assemblies are constructed with a small diameter in order to minimize cost and in order to avoid disadvantages typically incumbent in large diameter slip rings. The diameter, accordingly, is typically too small to encircle a patient. The slip ring assembly is, therefore, located at one end of the gantry assembly, and an arm is used to connect the slip ring assembly to the rotor of the x-ray assembly. The resultant gantry assembly forms a closed-bore into which the patient must be inserted, precluding access to the patient and intensifying patient concern. Moreover, such prior art gantry assemblies have minimal, if any, ability to tilt the plane in which the x-ray source rotates.

A gantry assembly might attempt to employ a large diameter slip ring to avoid the disadvantage of a close-bore configuration. In such a device, the x-ray assembly and slip ring assembly could be positioned side-by-side with fins or the like physically interconnecting the two assemblies. Once again, however, the ability to tilt the plane of the x-ray source is limited. To maximize the degree of possible tilt, the internal diameter of both the x-ray and slip ring assemblies must be increased, but with incumbent increase in bulk cost and complexity of the resultant gantry assembly. More importantly, for given rotor rotational speeds, surface speeds increase with larger diameter assemblies, which increases the probability of seal failure and the failure of other components. In known gantry assemblies, cost is further increased by utilizing separate ring bearing assemblies, stator structures and rotor structure, for both the x-ray assembly and the slip ring assembly.

It is, accordingly, an object of the present invention to provide a gantry assembly which allows for continuous rotation of an x-ray source in an economical and efficient manner.

A further object of the present invention is to provide a continuous rotation gantry assembly which has an open bore configuration with a minimal gantry cross-sectional area and overall volume, thus permitting unrestricted patient access.

A still further object of the present invention is to provide a continuous rotation gantry assembly which readily permits tilting of the plane in which an x-ray source rotates.

A still further object of the present invention is to provide a continuous rotation gantry assembly in which the x-ray source and x-ray optics may readily be aligned at a location remote from the gantry assembly.

A still further object of the present invention is to provide a continuous rotation gantry assembly which minimizes the likelihood of high voltage breakdown.

Another object of the present invention is to provide a continuous rotation gantry assembly containing liquid or gas insulation seals which are not subject to repeated failure and which are easily accessible for replacement in the unlikely event of failure.

Additional objects and advantages of the present invention will be set forth in part in the description which follows, and, in part, will be obvious from the description, or may be learned by practice of the invention. The objects and advantages of the invention may be realized and obtained by means of the instrumentalities and combinations particularly pointed out in the appended claims.

SUMMARY OF THE INVENTION

To achieve the foregoing objects, and in accordance with the purposes of the invention as embodied and broadly described herein, an integrated gantry assembly is provided which comprises (a) a stator having an opening along a longitudinal axis thereof of sufficient size to permit the stator to encircle a patient positioned along that axis, the stator being open along the axis to provide access to the patient from both sides of the stator; (b) a rotor having an opening along a longitudinal axis thereof of sufficient size to permit the rotor to encircle the patient positioned along its axis, the rotor being open along the axis to provide access to the patient from both sides of the rotor; (c) a bearing assembly located between the stator and rotor to align the stator and rotor coaxially and to support the rotor rotatably on the stator; (d) slip ring means mounted in part on the stator and in part on the rotor and located between the rotor and stator for effecting high voltage connection from the stator to the rotor while permitting continuous rotation of the rotor; and (e) x-ray means mounted onto and supported solely by the rotor.

Preferably, the inside surface of the stator which faces the patient generally lies along the surface of a truncated cone and the stator and rotor define between them first and second annular cavities. The first cavity preferably has a smaller diameter than the diameter of the second cavity and the cavities are offset one from the other along the longitudinal axes of the stator and rotor to permit one of the cavities to effectively house a negative electrode of the slip ring means and the other of the cavities to effectively house a positive electrode of the slip ring means without risk of breakdown or crossover between the negative and positive electrodes.

In the preferred embodiment illustrated, and stator and rotor have a cross section formed as a series of matching steps with a horizontal portion of at least two of the steps of the stator separated from an aligned horizontal portion of the steps of the rotor to form the two electrically and physically separated cavities mentioned above. It is also preferred that first and second seals be pancaked between the steps of the rotor and stator, with one seal located on each side of the above-mentioned cavities. It is still further preferable that the seals each be located by a respective seal retainer, and that the seal retainers be adjustably positionable to preload the seals, thereby controlling the amount of friction introduced to the gantry assembly by the seals and the amount of torque required to rotate the rotor of the gantry assembly.

Electrical connections are made to the cavities through vertical portions of the steps of the stator which define the cavities, wherein the axes of the electrical connectors are off-set from one another and parallel to the longitudinal axes of the rotor and stator. This orientation avoids the crossover encumbent in prior art slip rings and thereby eliminates the possibility of high voltage breakdown due to such crossover.

It is still further preferable that the x-ray means of the gantry assembly of the subject invention comprise: a bracket removably attached to the rotor; an x-ray source attached to the bracket; and x-ray optics also attached to the bracket, whereby the x-ray source and x-ray optics can be aligned on the bracket remote from the rotor and stator.

BRIEF DESCRIPTION OF THE DRAWINGS

The accompanying drawings, which are incorporated in and constitute a part of the specification, illustrate a preferred embodiment of the invention and, together with the general description of the invention given above and the detailed description of the preferred embodiment given below, serve to explain the principles of the invention.

DESCRIPTION OF THE PREFERRED EMBODIMENT

Figure 1:
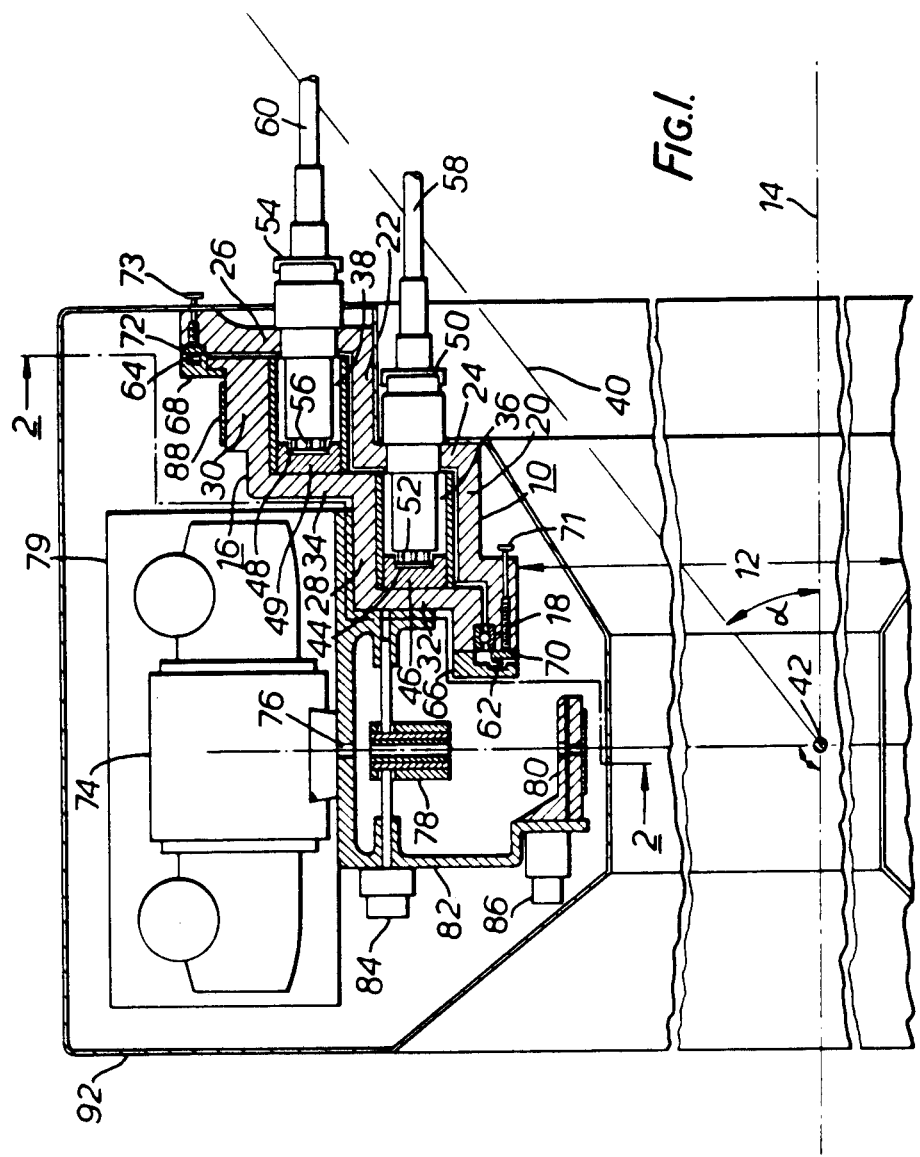
FIG. 1 is a cross-sectional, schematic representation of one section of the rotor and stator of a gantry assembly incorporating the teachings of the present invention.

Reference will now be made in detail to the present preferred embodiment of the invention as illustrated in the accompanying drawings.

In the drawings, there is illustrated a stator 10 having an opening 12 along a longitudinal axis 14 thereof of sufficient size to permit stator 10 to encircle a patient positioned along axis 14. Stator 10, being opened along axis 14, allows access to a patient from both sides of stator 10. A rotor 16 is illustrated as also having an opening 12 along the longitudinal axis 14, which axis is coincident with the axis of rotor 16. Rotor 16, accordingly, also provides access to the patient from both sides of the rotor. A bearing assembly 18 is located between stator 10 and rotor 16 to align stator 10 and rotor 16 coaxially along longitudinal axis 14 and to support rotor 16 rotatably on stator 10.

As illustrated, stator 10 preferably comprises a first cylindrical band section 20, second cylindrical band section 22, first disc section 24, and second disc section 26. First and second cylindrical band sections 20, 22 are coaxial with axis 14 and offset from one another along axis 14. First band section 20 has a smaller diameter than second band section 22. However, first band section 20 has a diameter sufficient to encircle a patient positioned along axis 14.

First and second disc sections 24 and 26 lie in planes perpendicular to axis 14. First disc section 24 extends perpendicularly from one edge of first band section 20 to one edge of second band section 22, and second disc section 26 extends perpendicularly from the other edge of second band section 22 in a direction away from axis 14.

Rotor 16 comprises a first cylindrical band section 28, a second cylindrical band section 30, a first disc section 32 and a second disc section 34. First and second cylindrical band sections 28 and 30 of rotor 16 are respectively aligned with and coaxial to first and second band sections 20 and 22 of stator 10. The diameter of first band section 28 is greater than the diameter of first band section 20, thereby forming a first cavity 36 therebetween. Likewise, second band section 30 of rotor 16 has a larger diameter than the diameter of second band section 22 of stator 10, thereby forming a second cavity 38 therebetween, with first disc section 24 of stator 10 closing off one side of cavity 36 and with second disc section 26 of stator 10 closing off one side of cavity 38.

First and second disc sections 32, 34 of rotor 16 lie in planes perpendicular to axis 14. First disc section 32 extends from one side of first band section 28 toward axis 14 to close off the other side of cavity 36, while second disc section 34 extends from the other edge of the first band section 28 of rotor 16 away from axis 14 to one edge of the second band section 30 of rotor 16 to close off the other side of cavity 38.

Accordingly, the longitudinal cross section of stator 10 and rotor 16 includes a series of matching steps with horizontal portions of the steps of the stator (band sections 20, 22) separated from aligned horizontal portions of the steps of the rotor (band sections 28, 30) to form two electrically and physically separated cavities therebetween, namely, cavities 36 and 38.

By construction of stator 10 in a step-like manner, the inside surface of stator 10 which faces a patient lying along axis 14 generally lies in the surface of a truncated cone illustrated by dotted line 40. Accordingly, stator 10 may be tilted about an axis 42 by an angle which approaches an angle formed by the intersection of axis 14 and dotted line 40. With ring bearing assembly 18 located as illustrated along first cylindrical band section 20, in combination with the use of the illustrated step-like configuration of stator 10, the degree of tilting permitted around axis 42 is maximized while the diameter of bearing assembly 18 is minimized.

In accordance with the integrated gantry assembly of the present invention, a slip ring is mounted in part on the stator of the gantry assembly and in part on the rotor of the gantry assembly for effecting high voltage connection from the stator to the rotor while permitting continuous rotation of the rotor. More specifically, as illustratively shown in FIG. 1, a first pancake electrode 44 in the form of a ring is mounted on first disc section 32 by means of an electrical insulator 46. A second pancake electrode 48 in the form of a ring is mounted to second disc section 34 of rotor 16 by means of an electrical insulator 49. A stator connector and brush block assembly 50 extends through first disc section 24 of stator 10 into cavity 36. Assembly 50 includes brushes 52 which contact ring 44 within cavity 36.

In a similar manner, stator connector and brush block assembly 54 extends through second disc section 26 of stator 10 into cavity 38. Brushes 56 on assembly 54 contact electrode ring 48. Although shown in FIG. 1 to be immediately adjacent to one another in FIG. 1, assemblies 50, 54 are preferably located some degrees from one another as shown in FIG. 2.

Figure 2:
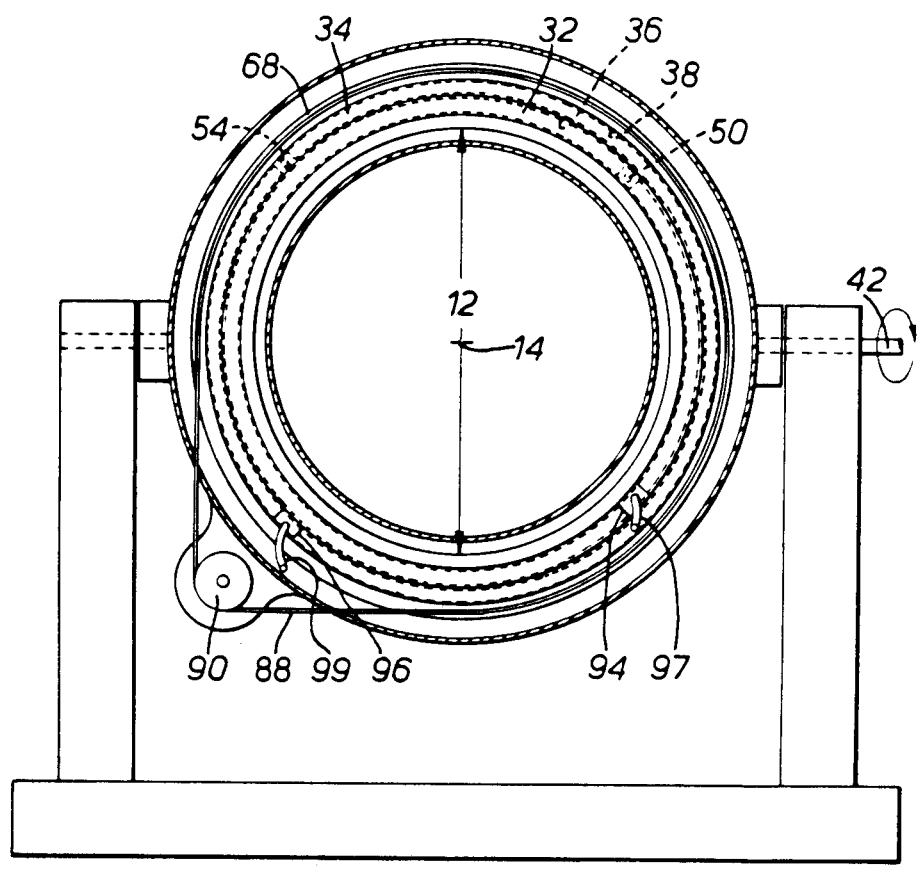
FIG. 2 is a sectional view of a schematic representation of a gantry assembly incorporating the teachings of the present invention.

Rotor high voltage connectors 96 and 94 are shown in FIG. 2 extending through discs 34 and 32, respectively, and are separated by some degrees from one another. The axes of assemblies 96 and 94 are also parallel to axis 14.

As a consequence of the matching step configurations of stator 10 and rotor 16 and the resultant formation of offset cavities 36 and 38, in combination with the use of pancake ring electrodes 44 and 48, the axes of assemblies 50, 54 are off-set from one another and parallel to axis 14. The high voltage electric cables 58, 60 are connected to assemblies 50, 54 which in turn are connected by poorly insulated conductors to the slip ring brushes 52, 56 without any kinks, bends or twists. This configuration avoids having any poorly insulated electrical conductors run adjacent, or cross directly over rings of any opposite polarity electrodes. A separation is instead provided between any such conductors and rings of opposite polarity electrodes, which avoids high voltage breakdown that can occur in standard large diameter prior art high voltage slip ring devices not having such separation. In a similar manner high voltage electric cables 97 and 99 are connected to assemblies 94 and 96, as shown in FIG. 2, which in turn are connected by poorly insulated conductors to rings 44 and 48 without any kinks, bends or twists. This configuration avoids having any poorly insulated electrical conductors run adjacent, or cross directly over rings of any opposite polarity electrodes. A separation is instead provided between any such electrical conductors and rings of opposite polarity electrodes which avoids high voltage breakdown that can occur in standard large diameter prior art high voltage slip ring devices not having such separation.

It is preferable that high voltage insulation in the form of an inert gas or liquid be introduced and held within cavities 36 and 38. To seal such liquid or gas within cavities 36 and 38, there is provided front slip ring seal 62 located on one side of cavities 36 and 38 and rear slip ring seal 64 located on the other side of cavities 36 and 38. More specifically, there are provided seal retainer rings 66, 68, one coupled to the front end of rotor 16 to house seal 62 and one coupled to the rear end of rotor 16 to house seal 64. Seal running surface 70 is coupled to the front end of stator 10 and mates against front slip ring 62. Seal running surface 72 is coupled to the front side of second disc section 26 of stator 10 and mates against ring seal 64. Retainers 66, 68 and running surfaces 70, 72 are readily accessible and may easily be removed and/or adjusted to either replace ring seals 62, 64 or adjust the preload to which these seals are exposed. Bolts 71 and 73 are illustrated in FIG. 1 as being adjustably attached to surfaces 70, 72 to readily adjust the location of these surfaces and, hence, adjust the preload to seals 62, 64. Accordingly, the life expectancy of slip ring seals 62, 64 is greatly increased over known prior art configurations.

Further in accordance with the present invention, there is provided x-ray means mounted onto and supported solely by the rotor of the integrated gantry assembly of the subject invention. As illustratively shown in FIG. 1, an x-ray assembly comprising an x-ray source 74, x-ray optics including a shutter assembly 76, wedge assembly 78, and a pre-patient collimator assembly 80 are all mounted on an x-ray mounting bracket 82. X-ray mounting bracket 82 is removably attachable to rotor 16, and when removed from rotor 16, bracket 82 permits alignment of the x-ray optics with x-ray source 74 remote from rotor 16 and stator 10. Moreover, with x-ray mounting bracket 82 affixed to rotor 16, either at first disc section 32 and/or at first cylindrical hand section 28, the x-ray source envelope 79 which defines the permissible location of x-ray source 74, may extend over first cylindrical band section 28 thereby minimizing the overall width of the resultant gantry assembly.

There is further illustrated in FIG. 1 a motor 84 to control positioning of wedge assembly 78, a motor 86 to control the opening of collimator assembly 80, a drive belt 88 on second cylindrical band section 30 which is coupled to a motor 90 (FIG. 2) which in turn is mounted on stator 10. A cover 92 is shown to encase the entire integrated gantry assembly.

The integrated gantry assembly of the subject invention accordingly provides for continuous rotation of an x-ray source through use of a high voltage slip ring to transmit high voltage power from stationary to rotating members. Unlike prior art slip ring assemblies, however, which are physically independent from the structures which supports the x-ray assembly, the support structures of the x-ray assembly, and of the slip ring assembly of the subject invention are integrated and supported by a single bearing assembly. The resultant structure is open bore and body concentric, and provides for a substantial amount of gantry tilt and substantial patient access. The subject invention is compatible with fourth generation CT scanner gantrys, and the combination of using a known fourth generation nutation approach in conjunction with the integrated slip ring of the subject invention provides for a very compact gantry design in comparison to conventional "black box" slip ring approaches.

The subject invention further incorporates an x-ray optics integration concept which stems from the desire to align all of the optics (i.e., shutter, collimator, wedges, etc.) on one fixture which may be carried away from the main gantry structure. This integration concept makes it more convenient to use an optical bench for optical device assembly and alignment rather than attempting assembly and optical alignment on a cumbersome scanner gantry. Previous fourth generation nutating scanners had been designed so that each optical device is independently mounted on the gantry, which requires independent alignment of each device on the gantry. The subject invention, accordingly, provides a significant advance over such prior art arrangements.

The incorporation of an integrated slip ring configuration permits the same large diameter ring bearings to support the x-ray optics and slip ring rotor, and permits a slip ring geometry which contours the outline of an x-ray source envelope for efficient utilization of space.

The slip ring stator casting has a second function as the gantry structural main frame which supports the rotor, rotor drive motor, and gantry covers and the like.

Separate anode and cathode chambers which are offset from one another minimize the possibility of high voltage breakdown. Moreover, the slip ring rotor casting has a second function, namely the structural support for x-ray optics, a heat exchanger, counterweights, and control electronics. The rotor casting may also act as a timing belt pulley for rotating the x-ray optics.

The rotor and stator castings of the subject invention act as Faraday shields.

The conical geometry of the slip ring assembly allows for a large internal diameter tunnel capable of substantial gantry tilting. This large diameter tunnel permits comfortable patient positioning even with 30° gantry tilting.

Replacement of both slip ring seals can be accomplished without separation of the rotor and stator sections.

It is also possible to rotate the brush assemblies with the rotor while maintaining the stationary slip rings attached to the stator which is the reverse of that shown in FIG. 1.

Additional advantages and modifications will readily occur to those skilled in the art. The invention in its broader aspects is, therefore, not limited to the specific details, representative apparatus, and illustrative examples shown and described. Accordingly, departures may be made from such details without departing from the spirit or scope of applicant's general inventive concept.

What is claimed is:

1. A gantry assembly comprising:
   a. a stator having:
      i. first and second cylindrical band sections coaxial to the axis of rotation of said assembly and offset from one another along said axis of rotation, said first band section having a smaller diameter than said second band section, yet having a diameter sufficient to encircle a patient positioned along said axis of rotation; and
      ii. first and second disc sections lying in planes perpendicular to said axis of rotation, said first disc section extending from one edge of said first band section to one edge of said second band section, and said second disc section extending from the other edge of said second band section in a direction away from said axis of rotation;
   b. a rotor having:
      i. first and second cylindrical band sections aligned with and coaxial to said first and second band sections of said stator, respectively, the diameters of said first and second band sections of said rotor being greater than the diameters of said first and second band sections of said stator, respectively, to form respective first and second annular cavities therebetween with said first disc section of said stator closing off one side of said first cavity and said second disc section of said stator closing off one side of said second cavity; and
      ii. first and second disc sections lying in planes perpendicular to said axis of rotation, said first disc section extending from one side of said first band section of said rotor to close off the other side of said first cavity and said second disc section extending from the other edge of said first band section of said rotor to one edge of said second band section of said rotor to close off the other side of said cavity;
   c. a bearing assembly located between said stator and said rotor to rotatably support said rotor on said stator; and
   d. first and second slip ring means mounted in part on said stator and in part on said rotor and exending into said first and second cavities, respectively, for effecting high voltage connection from said stator to said rotor while permitting continuous rotation of said rotor.

2. The integrated gantry assembly of claim 1 wherein first and second pancake electrodes are respectively mounted in said first and second cavities on said first and second disc sections of said rotor.

3. The integrated gantry assembly of claim 1 including positive and negative high voltage connectors extending one through said first disc section of said stator into said first cavity and one through said second disc section of said stator into said second cavity, the axes of said connectors lying parallel to said axis of rotation of said assembly.

* * * * *